(12) United States Patent
Sanderson et al.

(10) Patent No.: US 6,518,474 B1
(45) Date of Patent: Feb. 11, 2003

(54) PROCESS FOR PRODUCING ISOBUTYLENE FROM TERTIARY BUTYL ALCOHOL

(75) Inventors: John R. Sanderson, Austin, TX (US); Mark A. Mueller, Austin, TX (US)

(73) Assignee: Huntsman International LLC, Austin, TX (US)

( * ) Notice: Subject to any disclaimer, the term of this patent is extended or adjusted under 35 U.S.C. 154(b) by 0 days.

(21) Appl. No.: 09/692,021

(22) Filed: Oct. 19, 2000

Related U.S. Application Data

(60) Provisional application No. 60/162,598, filed on Oct. 29, 1999.

(51) Int. Cl.[7] .................................................. C07C 1/20
(52) U.S. Cl. ........................................ 585/639; 585/640
(58) Field of Search ................................. 585/639, 640

(56) References Cited

U.S. PATENT DOCUMENTS

| | | | | |
|---|---|---|---|---|
| 3,256,250 A | | 6/1966 | Frilette | 260/79.3 |
| 3,351,635 A | | 11/1967 | Kollar | 260/348.5 |
| 3,351,653 A | | 11/1967 | Carr et al. | 260/484 |
| 3,360,584 A | | 12/1967 | Kollar | 260/681 |
| 3,360,585 A | | 12/1967 | Winnick | 260/681 |
| 3,510,538 A | | 5/1970 | Rosenthal | 260/682 |
| 3,529,033 A | * | 9/1970 | Frilette et al. | 208/120.15 |
| 3,665,048 A | | 5/1972 | Grane et al. | 260/682 |
| 3,758,610 A | | 9/1973 | Turner | 260/681 |
| 3,836,603 A | | 9/1974 | Connor et al. | 260/673.5 |
| 3,860,662 A | | 1/1975 | Kollar | 260/618 C |
| 3,894,107 A | | 7/1975 | Butter et al. | 260/668 R |
| 4,058,576 A | | 11/1977 | Chang et al. | 260/673 |
| 4,144,138 A | | 3/1979 | Rao et al. | 203/46 |
| 4,155,945 A | | 5/1979 | Levine | 585/639 |
| 4,165,343 A | | 8/1979 | Levine et al. | 585/638 |
| 4,296,263 A | | 10/1981 | Worrell | 568/910 |
| 4,306,106 A | | 12/1981 | Kerr et al. | 585/640 |
| 4,547,598 A | | 10/1985 | Sanderson et al. | 568/922 |
| 4,547,601 A | | 10/1985 | Holland et al. | 585/310 |
| 4,704,482 A | | 11/1987 | Sanderson et al. | 568/922 |
| 4,705,903 A | | 11/1987 | Sanderson et al. | 568/922 |
| 4,742,179 A | | 5/1988 | Sanderson et al. | 568/913 |
| 4,845,251 A | | 7/1989 | Marquis et al. | 549/529 |
| 4,873,380 A | | 10/1989 | Sanderson et al. | 568/914 |
| 4,886,918 A | | 12/1989 | Sorensen et al. | 568/697 |
| 4,910,349 A | | 3/1990 | Sanderson et al. | 568/909.8 |
| 4,912,266 A | | 3/1990 | Sanderson et al. | 568/909.8 |
| 4,912,267 A | | 3/1990 | Sanderson et al. | 568/909.8 |
| 4,916,104 A | | 4/1990 | Isogai et al. | 502/213 |
| 4,922,033 A | | 5/1990 | Sanderson et al. | 568/909.8 |
| 4,922,034 A | | 5/1990 | Sanderson et al. | 568/909.8 |
| 4,967,020 A | | 10/1990 | Marier et al. | 568/896 |
| 5,081,318 A | | 1/1992 | Knifton | 568/698 |
| 5,102,428 A | | 4/1992 | Owen et al. | 44/448 |
| 5,157,192 A | | 10/1992 | Sorenson | 585/640 |
| 5,185,480 A | | 2/1993 | Sanderson et al. | 568/913 |
| 5,191,143 A | | 3/1993 | Su et al. | 585/640 |
| 5,243,091 A | | 9/1993 | Kruse et al. | 568/697 |
| 5,292,964 A | | 3/1994 | Gupta | 568/697 |
| 5,313,006 A | * | 5/1994 | Knifton | 568/698 |
| 5,354,912 A | | 10/1994 | Hwan et al. | 568/697 |
| 5,354,917 A | | 10/1994 | Sanderson et al. | 568/909.8 |
| 5,364,981 A | | 11/1994 | Knifton et al. | 568/698 |
| 5,386,065 A | | 1/1995 | Kruse et al. | 568/698 |
| 5,387,721 A | | 2/1995 | Kruse et al. | 568/697 |
| 5,395,982 A | | 3/1995 | Cassata et al. | 568/699 |
| 5,457,243 A | | 10/1995 | Knifton et al. | 568/697 |
| 5,723,698 A | | 3/1998 | Dai et al. | 568/913 |
| 5,811,620 A | | 9/1998 | Knifton et al. | 585/639 |
| 5,856,588 A | * | 1/1999 | Dai et al. | 568/671 |
| 5,939,592 A | | 8/1999 | Knifton et al. | 568/877 |
| 6,133,484 A | | 10/2000 | Knifton et al. | 568/698 |

FOREIGN PATENT DOCUMENTS

| | | |
|---|---|---|
| JP | 63101337 | 5/1988 |
| WO | WO 99/24384 | 5/1999 |

OTHER PUBLICATIONS

Ponec and Bond, Catalysis by Metals and Alloys, pp. 520–524; Elsevier; Amsterdam, 1995.

Bobylev et al., "A New Method for the Production of Alcohols by Catalytic Cleavage," J. Organic Chem. of the USSR, 21(5, Part 2): 1028–1029, 1985.

Zahalka, et al., "Rhodium Cabonyl–2–Methoxyethanol. An Effective Catalytic System for the Decarbonylation of Formate Esters," Tetrahedron Letters, vol. 28, No. 20, pp. 2215–2216, Elsevier Science Publishers, Amsterdam, NL (1987).

Vanhoye, et al, "Rhodium–Catalyzed Reductive Carbonylation of Methyl Formate to Acetaldehyde," Angewandte Chemie, International Edition in English, vol. 27, No. 5, pp. 683–684 Verlag Chemie, Weinheim, DE (May 1988).

Nurberdiev, et al., "Transformations of Alcohol and Glycol Formates Initiated by Organic Hydroperoxides," Doklady Chemistry, vol. 296, No. 9, pp. 418–419 Consultants Bureau, New York, US (Sep. 1987).

* cited by examiner

*Primary Examiner*—Walter D. Griffin
(74) *Attorney, Agent, or Firm*—O'Keefe, Egan & Peterman LLP

(57) ABSTRACT

A process for producing substantially pure isobutylene containing relatively small amounts of higher oligomer byproducts. The process may employ a Y-zeolite catalyst having a silica to alumina ratio of less than or equal to about ten.

39 Claims, No Drawings

PROCESS FOR PRODUCING ISOBUTYLENE FROM TERTIARY BUTYL ALCOHOL

The present application claims priority on co-pending U.S. provisional patent application serial No. 60/162,598 filed on Oct. 29, 1999, the entire text and all contents of which is specifically incorporated herein by reference.

BACKGROUND OF THE INVENTION

1. Field of the Invention

Disclosed is a process for producing isobutylene by the dehydration of tertiary butyl alcohol, and more particularly to a process for producing substantially pure isobutylene containing no or relatively small amounts of higher oligomer byproducts. In one particular embodiment, disclosed is a process for producing substantially pure isobutylene by dehydration of tertiary butyl alcohol in the presence of a Y-zeolite catalyst having a silica to alumina ratio of less than or equal to about ten.

2. Description of the Related Art

Isobutane may be reacted with oxygen to form a peroxidation reaction product containing tertiary butyl hydroperoxide and tertiary butyl alcohol, along with minor amounts of acetone, methanol, various esters and acids. One typical use of tertiary butyl hydroperoxide manufactured in this manner is to produce epoxides. For example, the process for the manufacture of substituted epoxides from alpha-olefins such as propylene is discussed in U.S. Pat. No. 3,351,635. In this process, an organic hydroperoxide such as tertiary butyl hydroperoxide may be reacted with an olefinically unsaturated compound such as propylene in the presence of a soluble molybdenum catalyst. Products of this reaction include propylene oxide and tertiary butyl alcohol.

In one conventional vapor phase process, tertiary butyl alcohol may be used to produce isobutylene by way of a vapor phase reaction at very high temperatures, i.e., from about 350 to about 450° C. Such conventional vapor phase processes typically are accompanied by a large consumption of energy and require expensive heating equipment and other costly hardware.

In one conventional liquid phase process for the dehydration of tertiary butyl alcohol, azeotroping agents, such as benzene or xylene, are used to remove water from the liquid phase reaction product. However, azeotroping agents are typically expensive and may cause production of relatively heavy molecular weight products that must be purged from the process system. Examples of such conventional liquid phase products are described in, for example, U.S. Pat. Nos. 4,165,343 and 4,155,945.

Other conventional processes for the dehydration of tertiary butyl alcohol include those processes employing ion exchange resins. One example of such a process for the dehydration of X tertiary butyl alcohol is described in U.S. Pat. No. 3,256,250. This process employs sulfonated and nitrated styrene divinyl benzene resin which may be utilized to produce isobutylene. U.S. Pat. No. 3,510,538 describes a process in which tertiary butyl alcohol is continuously dehydrated over a cation exchange resin with water formed during the process being continuously removed to increase dehydration rates. However, cation exchange resins are expensive, and typically cannot be operated at temperatures greater than about 110° C. to about 120° C. Furthermore, to obtain useful rates of dehydration and relatively high conversion percentages, water must be continuously removed from the system.

Other conventional process for the dehydration of tertiary butyl alcohol are employed to produce higher molecular weight conversion products. For example, U.S. Pat. No 5,157,192 describes a process for the conversion of tertiary butyl alcohols to C-8 olefins over certain zeolite catalysts, such as certain beta-zeolites. In this process, tertiary butyl alcohol may be converted to 2,2,4-trimethylpentane (diisobutylene). A two-step partial oxidation-dimerization process to yield C-8 olefins is described.

SUMMARY OF THE INVENTION

Disclosed herein is a process for producing isobutylene from tertiary butyl alcohol in the presence of Y-zeolites. Using the disclosed process, tertiary butyl alcohol may be dehydrated at relatively low temperatures and pressures to produce isobutylene in substantially quantitative yield with little or substantially no diisobutylene formed. Surprisingly, these results may be achieved using zeolites having a silica to aluminum ratio of less than about 10, and in the presence of water in the process. Advantageously, the disclosed method obtains good conversion of tertiary butyl alcohol with relatively low silica to alumina ratio. Low silica to alumina ratio zeolite catalysts typically cost less and are more readily available than zeolite catalysts having higher silica to alumina ratios.

Using the disclosed process, substantially high yields of isobutylene may be produced in the substantial absence of dimer byproducts, such as diisobutylene. Such substantially high yield isobutylene products may be advantageously produced for use, for example, in plants where it is desirable to reduce isobutylene to isobutane and recycle it. For example, isobutane may be recycled to a peroxidation reactor to make more tert-butylhydroperoxide. The tert-butylhydroperoxide may be used (with propylene) in the presence of a molybdenum catalyst to produce more propylene oxide and tert-butylalcohol. The tert-butylalcohol may then be recycled to the above process. Other end uses for which substantially high purity isobutylene product of the disclosed process may be employed include, but are not limited to, for the production of substantially high purity isobutylene for sale to polymer markets, and where it is desirable to produce a mixture of isobutylene and isobutane for alkylation.

Whether a tertiary butyl alcohol-containing feed stream contains a relatively large amount of other components or is substantially pure tertiary butyl alcohol, relatively high conversion of tertiary butyl alcohol and relatively high selectivity to isobutylene may be advantageously achieved using the disclosed method. One or more other advantages of embodiments of the disclosed method include, but are not limited to, no need for large consumption of energy and/or expensive heating equipment as required with high temperature conventional processes, no need for expensive azeotroping agents or purge of relatively heavy molecular weight azeotrope products that must be purged from the process system, no requirement for continuous removal of water from the system, etc.

In one respect, disclosed is a method of producing isobutylene, including: contacting tertiary butyl alcohol with a Y-zeolite catalyst to produce isobutylene; wherein the Y-zeolite catalyst may have a silica to alumina ratio of less than about 10. The contacting may occur as part of a batch process (e.g., in a kettle or any other batch process reaction vessel suitable for producing isobutylene from tertiary butyl alcohol using Y-zeolite catalysts as described herein), or as part of a continuous flow process employing a feed stream that includes tertiary butyl alcohol (e.g., in any continuous flow process reaction vessel suitable for producing isobutylene from tertiary butyl alcohol using Y-zeolite catalysts as described herein). In one embodiment, water may also be present with tertiary butyl alcohol in a batch process reaction vessel or continuous flow feed stream. In another embodiment, a feed stream may include from about 70% to about 100% by weight tertiary butyl alcohol by total weight of the feed stream. In m another embodiment, the feed stream may include from about 70% to less than about 100% by weight tertiary butyl alcohol by total weight of the feed stream, and from greater than about 0% to about 30% by weight water by total weight of the feed stream. In another embodiment, conversion of tertiary butyl alcohol may be from about 80% to about 100%, and selectivity to isobutylene may be from about 85% to about 100%.

In another respect, disclosed is a method of producing isobutylene, including: contacting a feed stream including tertiary butyl alcohol and water with a Y-zeolite catalyst to produce isobutylene; wherein the Y-zeolite catalyst may have a silica to alumina ratio of less than or equal to about 10; wherein the contacting occurs within a reaction vessel at a temperature of greater than or equal to about 140° C., a pressure of from about 50 psig to 1000 psig, and a liquid hourly space velocity ("LHSV") of from about 0.1 g/mL catalyst/hour to about 20.0 g/mL catalyst/hour; wherein conversion of tertiary butyl alcohol may be from about 80% to about 100%, and wherein selectivity to isobutylene may be from about 85% to about 100%. In one embodiment, the Y-zeolite catalyst may have a silica to alumina ratio of from about 5 to about 10, and in another embodiment from about 5 to about 6. In another embodiment, the contacting may occur at a temperature of from about 140° C. to about 250° C., and in yet another embodiment from about 180° C. to about 250° C. In yet another embodiment, conversion of tertiary butyl alcohol may be from about 90% to about 100%. In yet another embodiment, selectivity to isobutylene may be from about 95% to about 100%. In yet another embodiment, the contacting may occur at a temperature of from about 200° C. to about 250° C. In yet another embodiment, conversion of tertiary butyl alcohol may be from about 95% to about 100% and selectivity to isobutylene may be from about 95% to about 100%.

In another respect, disclosed is a method of producing isobutylene, including: contacting a feed stream comprising tertiary butyl alcohol and water with a Y-zeolite catalyst to produce isobutylene; wherein the Y-zeolite catalyst has a silica to alumina ratio of from about 5 to about 6; wherein the contacting occurs within a reaction vessel at a temperature of from about 140° C. to about 200° C., a pressure of from about 240 psig to about 275 psig, and a LHSV of from about 1 g/mL catalyst/hour to about 5 g/mL catalyst/hour; and wherein conversion of tertiary butyl alcohol is from about 80% to about 100%, and wherein selectivity to isobutylene is from about 85% to about 100%.

DESCRIPTION OF ILLUSTRATIVE EMBODIMENTS

Catalysts suitable for use in the disclosed process include Y-zeolites having a $SiO_2/Al_2O_3$ molar ratio ("silica to alumina ratio") of less than or equal to about 10, alternatively of less than or equal to about 5. In one embodiment, Y-zeolites having a silica to alumina ratio of from about 1 to about 10, alternatively from about 5 to about 10, and further alternatively from about 5 to about 6, may be employed. In separate respective and alternative embodiments, Y-zeolites having a silica to alumina ratio in a range of from about x to about y may be employed, where for each respective embodiment the value of x may be selected from the range of values of from 0.1 to 10 and a corresponding value of y may selected from the range of values of from 0.1 to 10, with the proviso that x not equal y for a given embodiment.

Suitable Y-zeolite catalysts include any Y-zeolite or mixture of Y-zeolites effective to catalyze the conversion of tertiary butyl alcohol to isobutylene, and that has or have silica to alumina ratios as described elsewhere herein. Examples of specific suitable Y-zeolites include, but are not limited to, "ZEOLIST CBV-300", "ZEOLIST CBV-400", "ZEOLIST CBV-500" (available from the Zeolist Corporation); "UOP LZY-84"; "UOP LZY-64 available from UOP, and Engelhard "LY-ZEOLITE" from Engelhard Corporation.

Suitable feed stocks for use in the disclosed process include, but are not limited to, any process stream containing tertiary butyl alcohol. Such a feed stock stream may be substantially pure tertiary butyl alcohol, or may contain tertiary butyl alcohol mixed with other components. For example, in one embodiment, a feed stock may be the effluent from a tertiary butyl alcohol/propylene oxide production facility, such as described in U.S. Pat. Nos. 4,873,380, 4,845,251, 4,742,179, and 4,704,482, which are incorporated herein by reference. Such an effluent stream contains mainly tertiary butyl alcohol, but may also contain impurities such as acetone, methanol, various acids and esters, as well as water. In this regard, water is typically present in tertiary butyl alcohol effluent as it comes from a tertiary butyl alcohol/propylene oxide plant. Thus, it will be understood with benefit of this disclosure that types of tertiary butyl alcohol-containing feed streams that may be treated using the disclosed method may contain tertiary butyl alcohol in relatively small amounts up to substantially pure tertiary butyl alcohol.

In any case, the disclosed method maybe employed to achieve relatively high conversion of any tertiary butyl alcohol content present in the feed stream with high conversion rates to isobutylene relative to conventional processes. In one embodiment, tertiary butyl alcohol content in the feed stream may range from about 50% to about 100% by weight of feed, alternatively from about 50% to about 75% by weight of feed. In another embodiment, tertiary butyl alcohol content in the feed stream may range from about 75% to about 99.99%, alternatively from about 75% to about 90% by weight of feed. In yet another embodiment, tertiary butyl alcohol content in the feed stream may range from about 95% to about 99.99% by weight of feed. In yet another embodiment, tertiary butyl alcohol content in the feed stream may range from about 70% to about 100% by weight of feed. In one embodiment, amounts of water which may be present in such a tertiary butyl alcohol-containing feed stream may range from substantially no water up to about 30% of water by weight of feed, or alternatively, from about 5% to about 20% of water by weight of feed. In another embodiment, amounts of water which may be present in such a tertiary butyl alcohol-containing feed stream may range from about .01% to about 10% of water by weight of feed. It will be understood with benefit of this disclosure that each of the preceding concentration ranges for feed stream components are exemplary only, and amounts of each of the indicated components may fall outside these ranges. Furthermore, it will be understood that other components may be present as well.

Process conditions which may be employed in the practice of the disclosed method include any effective conditions (e.g., temperature, pressure, process flow rate relative to catalyst, etc.) at which tertiary butyl alcohol may be converted to isobutylene using one or more of the disclosed Y-zeolite catalysts. In this regard, the disclosed method may be practiced as a liquid or vapor phase reaction.

In one embodiment, relatively low pressures and/or temperatures may be employed to enhance tertiary butyl alcohol conversion and selectivity to isobutylene. For example, process temperature may range from about 50° C. to about 250° C., alternatively from about 120° C. to about 220° C., alternatively from about 140° C. to about 190° C., alternatively from about 140° C. to about 180° C., alternatively from about 160° C. to about 220° C, alternatively from about 160° C. to about 200° C., alternatively from about 160° C. to about 190° C., and further alternatively from about 160° C. to about 180° C. In another embodiment, process temperature may range from about 160° C. to about 250° C., alternatively from about 180° C. to about 250° C., alternatively from about 180° C. to about 220° C., and further alternatively from about 180° C. to about 200° C. In another embodiment, process pressure may range from about 50 psig to 1000 psig, alternatively from about 100 psig to about 300 psig, alternatively from about 200 psig to about 300 psig, alternatively from about 240 psig to about 280 psig, alternatively from about 240 psig to about 275 psig, alternatively from about 260 psig to about 280 psig, alternatively from about 260 psig to about 275 psig, and further alternatively from about 260 psig to about 270 psig. Flow rates of tertiary butyl alcohol-containing feed stream relative to the disclosed Y-zeolite catalyst may range from about 0.1 g/mL catalyst/hour to about 20 g/mL catalyst/hour, alternatively from about 1.0 g/mL catalyst/hour to about 10.0 g/mL catalyst/hour, and further alternatively from about 1.0 g/mL catalyst/hour to about 5.0 g/mL catalyst/hour. However, process conditions outside these ranges are also possible. Furthermore, various combinations of the above pressure ranges, temperature ranges and/or flow rate ranges are possible, as so desired.

In one embodiment of the disclosed method and Y-zeolite catalysts, conversion of tertiary butyl alcohol (i.e., moles of tertiary butyl alcohol converted during reaction expressed as a percentage of moles of tertiary butyl alcohol originally present) may be from about 50% to about 100%, alternatively from about 60% to about 100%, alternatively from about 70% to about 100%, alternatively from about 80% to about 100%, alternatively from about 90% to about 100%, and further alternatively from about 95% to about 100%. In another embodiment, selectivity to isobutylene (i.e., moles of isobutylene formed during reaction expressed as a percentage of moles of tertiary butyl alcohol converted during reaction) may be from about 70% to about 100%, alternatively from about 80% to about 100%, alternatively from about 85% to about 100%, alternatively from about 88% to about 100%, alternatively from about 90% to about 100%, and further alternatively from about 95% to about 100%. However, conversion values and/or selectivity values outside these ranges are also possible. Furthermore, various combinations of the above conversion values and selectivity values are possible using embodiments of the disclosed method and catalysts.

It will be understood with benefit of this disclosure that in the practice of the disclosed method virtually any reaction scheme and/or any type of reaction vessel suitable for contacting tertiary butyl alcohol with the disclosed Y-zeolite catalyst may be employed, including batch and continuous flow methods. In one continuous reaction scheme embodiment, a tubular reaction vessel containing a fixed bed of the disclosed Y-zeolite catalyst may be employed, and operated in a single-pass mode or with one or more effluent recycle streams. Furthermore, one or more reaction vessels may be employed, with multiple reaction vessels operated in series and/or parallel. Continuous flow reaction vessels may be configured with any suitable flow direction, e.g., upflow, downflow, etc.

It will be understood by benefit of this disclosure that a continuous process scheme may be employed without a recycle stream using fractionation equipment, or may be employed with an unreacted tertiary butyl alcohol recycle stream in the absence of such fractionation equipment. When an unreacted tertiary butyl alcohol recycle stream is employed, water content may be increased in the reaction vessel.

EXAMPLES

The following examples are illustrative and should not be construed as limiting the scope of the invention or claims thereof.

In each of the following experiments, 100 ml of the indicated catalyst was charged to a 100 ml electrically heated stainless-steel upflow reactor. A tertiary butyl alcohol-containing feed stream containing 86.7% by weight tertiary butyl alcohol ("TBA"), 10.5% water, 1.9% acetone, 0.4% methanol, and small amounts of acid from esters was employed. In each example, the feed was pumped through the reactor at the desired rate (grams/hour) and the temperature was raised until the specified temperature was reached. When the temperature had stabilized, the feed was pumped through the reactor for several hours, and then a 300 gram to 600 gram sample collected in a stainless steel bomb. Water and organic phases were present in each sample and were separated and weighed. Compositional analyses of each phase was determined using a gas chromatograph. Conversion and selectivities were calculated based on these analyses. Selectivities may be taken to equal 100% in those cases where selectivity values greater than 100.0% were calculated from experimental data.

As used in the following examples, "n.d." means "not determined."

| Comparative Example A - Utilizing Strongly Acidic Sulfidic Cationic Catalyst ("AMBERLYST ® - 15") | | | | | |
|---|---|---|---|---|---|
| Tertiary Butyl Alcohol (g/hr) | Reaction Pressure (psig) | Reaction Temp. (° C.) | Tertiary Butyl Alcohol Conversion (%) | Selectivity, (%) | |
| | | | | Isobutylene | Diisobutylene |
| 125 | 243 | 90 | 15.5 | 99.4 | 0.0 |
| 125 | 262 | 100 | 19.7 | 105.7 | 0.0 |
| 120 | 256 | 110 | 23.8 | 102.1 | 0.0 |
| 120 | 265 | 120 | 29.2 | 100.9 | 0.0 |

The results of comparative Example A show that using a strongly acidic sulfidic cationic catalyst under the indicated conditions, tertiary butyl alcohol conversion of a tertiary butyl alcohol-containing feed stream that includes water was limited to less than 30%.

Comparative Example B - UOP BetaZeolite Catalyst with Silica/Alumina Ratio of 22.1

| Tertiary Butyl Alcohol (g/hr) | Reaction Pressure (psig) | Reaction Temp. (°C.) | Tertiary Butyl Alcohol Conversion (%) | Selectivity, (%) Isobutylene | Diisobutylene |
|---|---|---|---|---|---|
| 125 | 283 | 120 | 55.2 | 52.9 | 48.4 |
| 130 | 264 | 143 | 95.7 | 38.6 | 51.6 |
| 126 | 265 | 163 | 96.5 | 32.8 | 39.4 |
| 122 | 257 | 182 | 95.6 | 70.8 | 21.8 |

The results of comparative Example B show that the BetaZeolite used above under the indicated conditions achieved a tertiary butyl alcohol conversion of greater than 95% at 143° C. to 180° C. but with poor selectivity to isobutylene. In some cases, greater than 50% selectivity to diisobutylene was observed. When diisobutylene content is observed, often higher oligomers are also present.

Comparative Example C - Zeolist "CBV 28014G" ZSM-5 Catalyst with Silica/Alum Ratio of 280

| Tertiary Butyl Alcohol (g/hr) | Reaction Pressure (psig) | Reaction Temp. (°C.) | Tertiary Butyl Alcohol Conversion (%) | Selectivity, (%) Isobutylene | Diisobutylene |
|---|---|---|---|---|---|
| 115 | 246 | 121 | 26.7 | 98.4 | 0.1 |
| 132 | 267 | 142 | 15.6 | 109.2 | 0.0 |
| 128 | 279 | 161 | 55.4 | 101.6 | 0.0 |
| 121 | 273 | 179 | 90.1 | 94.0 | 0.0 |

The results of comparative Example C show conversions and selectivities achieved under the indicated conditions with a ZSM-5 catalyst having a relatively high silica to alumina ratio of 280.

Comparative Example D - Zeolist "CBV 780" Catalyst with Silica/Alumina Ratio of 80

| Tertiary Butyl Alcohol (g/hr) | Reaction Pressure (psig) | Reaction Temp. (°C.) | Tertiary Butyl Alcohol Conversion (%) | Selectivity, (%) Isobutylene | Diisobutylene |
|---|---|---|---|---|---|
| 125 | 287 | 120 | 28.1 | 105.0 | n.d. |
| 125 | 284 | 140 | 77.1 | 90.5 | 10.1 |
| 125 | 290 | 160 | 88.2 | 77.9 | 9.3 |
| Approx 125 | Approx 290 | 180 | 89 | 88.4 | 5 |

The results of comparative Example D show that under the indicated conditions the Y-Zeolite used above achieved relatively high selectivity to isobutylene at 120° C., but with relatively low tertiary butyl alcohol conversion of less than 30%. At higher temperatures, tertiary butyl alcohol conversion was higher, but isobutylene selectivity dropped to as low as approximately 78%, with an increase in selectivity to diisobutylene. As previously mentioned, when diisobutylene content is observed, often higher oligomers are also present.

The following additional Comparative Examples E–G are also provided.

Comparative Example E - Zeolist "21A" (Mordenite) Catalyst with Silica/Alumina Ratio of 20

| Tertiary Butyl Alcohol (g/hr) | Reaction Pressure (psig) | Reaction Temp. (°C.) | Tertiary Butyl Alcohol Conversion (%) | Selectivity, (%) Isobutylene | Diisobutylene |
|---|---|---|---|---|---|
| 120 | 285 | 120 | 17.3 | 105.6 | n.d. |
| 125 | 249 | 140 | 46.6 | 104.8 | n.d. |

-continued

Comparative Example E - Zeolist "21A" (Mordenite) Catalyst with Silica/Alumina Ratio of 20

| Tertiary Butyl Alcohol (g/hr) | Reaction Pressure (psig) | Reaction Temp. (° C.) | Tertiary Butyl Alcohol Conversion (%) | Selectivity, (%) | |
|---|---|---|---|---|---|
| | | | | Isobutylene | Diisobutylene |
| 120 | 260 | 160 | 76.3 | 109.6 | n.d. |
| 120 | 273 | 180 | 55.4 | 73.1 | n.d. |

Comparative Example F - Zeolist "CBV 1502" ZSM-5 Catalyst with Silica/Alumina Ratio of 150

| Tertiary Butyl Alcohol (g/hr) | Reaction Pressure (psig) | Reaction Temp. (° C.) | Tertiary Butyl Alcohol Conversion (%) | Selectivity, (%) | |
|---|---|---|---|---|---|
| | | | | Isobutylene | Diisobutylene |
| 120 | 252 | 100 | 19.5 | 104.7 | n.d. |
| 120 | 264 | 120 | 31.0 | 100.9 | n.d. |
| 125 | 238 | 140 | 74.2 | 99.8 | n.d. |
| 120 | 237 | 160 | 76.2 | 104.9 | n.d. |
| 120 | 240 | 180 | 78.3 | 105.6 | n.d. |

Comparative Example G - Zeolist "CBV 8062" ZSM-5 Catalyst with Silica/Alumina Ratio of 80

| Tertiary Butyl Alcohol (g/hr) | Reaction Pressure (psig) | Reaction Temp. (° C.) | Tertiary Butyl Alcohol Conversion (%) | Selectivity, (%) | |
|---|---|---|---|---|---|
| | | | | Isobutylene | Diisobutylene |
| 125 | 263 | 120 | 24.9 | 87.7 | n.d. |
| 120 | 274 | 140 | 74.1 | 97.6 | n.d. |
| 125 | 275 | 160 | 83.4 | 96.1 | n.d. |
| 120 | 258 | 180 | 90.6 | 98.2 | n.d. |

Example 1 - Y-zeolite with Silica to Alumina Ratio of 5.1 (ZEOLIST "CBV-300")

| Tertiary Butyl Alcohol (g/hr) | Reaction Pressure (psig) | Reaction Temp. (° C.) | Tertiary Butyl Alcohol Conversion (%) | Selectivity, (%) | |
|---|---|---|---|---|---|
| | | | | Isobutylene | Diisobutylene |
| 129 | 258 | 140 | 29.8 | 96.0 | 0.0 |
| 119 | 240 | 161 | 80.7 | 98.7 | 0.0 |
| 123 | 257 | 180 | 85.8 | 98.9 | 0.0 |

The results of Example 1 show excellent conversion (81% to 86%) of tertiary butyl alcohol at 161° C. to 180° C. and under the other indicated conditions using the disclosed Y-zeolite catalyst. In addition, no detectable diisobutylene was formed. Thus, using the disclosed method and catalyst, excellent tertiary butyl alcohol conversion and excellent selectivity to isobutylene may be realized with a catalyst having a relatively low silica to alumina ratio of less than 10.

Example 2 - Y-zeolite with Silica to Alumina Ratio of 5.1 (ZEOLIST "CBV-400")

| Tertiary Butyl Alcohol (g/hr) | Reaction Pressure (psig) | Reaction Temp. (° C.) | Tertiary Butyl Alcohol Conversion (%) | Selectivity, (%) | |
|---|---|---|---|---|---|
| | | | | Isobutylene | Diisobutylene |
| 125 | 269 | 120 | 12.9 | 104.3 | 0.0 |
| 123 | 272 | 140 | 31.0 | 96.0 | 0.1 |
| 123 | 264 | 160 | 91.7 | 98.8 | 0.0 |
| 120 | 269 | 182 | 92.1 | 91.2 | 4.7 |

The results of Example 2 show excellent tertiary butyl alcohol conversion (about 92%) at 160° C. to 182° C. and under the other indicated conditions using the disclosed Y-zeolite catalyst. In addition, only a small amount of diisobutylene was formed at the higher temperatures. As with Example 3, using the disclosed method and catalyst, excellent tertiary butyl alcohol conversion and excellent selectivity to isobutylene may be realized with a catalyst having a relatively low silica to alumina ratio.

under the other indicated conditions using the disclosed Y-zeolite catalyst with relatively low silica to alumina ratio. In addition, only a small amount of diisobutylene was formed at the higher temperatures.

The following additional Examples 4–7 are also provided.

Example 3 - Y-zeolite with Silica to Alumina Ratio of 5.1 (ZEOLIST "CBV-500")

| Tertiary Butyl Alcohol (g/hr) | Reaction Pressure (psig) | Reaction Temp. (° C.) | Tertiary Butyl Alcohol Conversion (%) | Selectivity, (%) Isobutylene | Diisobutylene |
|---|---|---|---|---|---|
| 119 | 271 | 121 | 21.4 | 96.8 | 0.0 |
| 122 | 266 | 141 | 68.7 | 105.4 | 0.0 |
| 122 | 262 | 162 | 89.6 | 95.5 | 0.0 |
| 119 | 266 | 187 | 92.6 | 101.0 | 1.1 |

The results of Example 3 show excellent tertiary butyl alcohol (about 90 to 93%) at about 140° C. to 187° C. and Example 4 - Y-zeolite with Silica to Alumina Ratio of 5.1 (ZEOLIST "CBV-500")

| Tertiary Butyl Alcohol (g/hr) | Reaction Pressure (psig) | Reaction Temp. (° C.) | Tertiary Butyl Alcohol Conversion (%) | Selectivity, (%) Isobutylene | Diisobutylene |
|---|---|---|---|---|---|
| 168 | 261 | 184 | 86.4 | 101.4 | 0.1 |
| 152 | 262 | 199 | 95.0 | 101.6 | 0.0 |
| 151 | 260 | 180 | 81.6 | 101.9 | 0.0 |
| 157 | 260 | 200 | 96.6 | 99.2 | 0.0 |
| 198 | 249 | 179 | 70.6 | 104.2 | 0.1 |
| 203 | 259 | 200 | 97.4 | 100.9 | 0.0 |
| 300 | 251 | 179 | 68.0 | 88.6 | 0.1 |
| 300 | 259 | 200 | 96.5 | 96.5 | 0.0 |

Example 5 - Y-zeolite with Silica to Alumina Ratio of 5.1 (ZEOLIST "CBV-500")

| Tertiary Butyl Alcohol (g/hr) | Reaction Pressure (psig) | Reaction Temp. (° C.) | Tertiary Butyl Alcohol Conversion (%) | Selectivity, (%) Isobutylene | Diisobutylene |
|---|---|---|---|---|---|
| 300 | 247 | 141 | 38.0 | 100.2 | 0.0 |
| 308 | 244 | 159 | 73.8 | 88.2 | 1.1 |
| 304 | 248 | 183 | 92.3 | 102.8 | 0.0 |
| 305 | 247 | 183 | 91.2 | 103.3 | 0.0 |
| 304 | 244 | 141 | 40.3 | 100.4 | 0.0 |
| 313 | 250 | 184 | 79.1 | 103.2 | 0.0 |
| 310 | 254 | 140 | 43.9 | 102.7 | 0.0 |
| 292 | 252 | 160 | 79.6 | 102.4 | 0.0 |
| 300 | 250 | 180 | 91.4 | 101.3 | 0.3 |

Example 6 - Y-zeolite with Silica to Alumina Ratio of 5.9 (UOP "LZY-84")

| Tertiary Butyl Alcohol (g/hr) | Reaction Pressure (psig) | Reaction Temp. (° C.) | Tertiary Butyl Alcohol Conversion (%) | Selectivity, (%) Isobutylene | Diisobutylene |
|---|---|---|---|---|---|
| 103 | 249 | 180 | 91.5 | 102.2 | 1.4 |
| 203 | 259 | 140 | 54.9 | 101.7 | 0.5 |
| 212 | 260 | 160 | 83.3 | 102.5 | 0.6 |
| 202 | 261 | 181 | 90.9 | 102.8 | 0.6 |
| 296 | 264 | 141 | 49.3 | 104.3 | 0.3 |
| 291 | 263 | 160 | 77.2 | 96.9 | 0.5 |
| 322 | 266 | 180 | 90.9 | 111.0 | 0.3 |
| 402 | 272 | 181 | 82.4 | 102.5 | 0.3 |
| 436 | 275 | 179 | 79.7 | 98.9 | 0.3 |
| 119 | 240 | 161 | 80.7 | 98.7 | 0.0 |
| 123 | 257 | 180 | 85.8 | 98.9 | 0.0 |

Example 7 - Y-zeolite with Silica to Alumina Ratio of 5.9 (UOP "LZY-84")

| Tertiary Butyl Alcohol (g/hr) | Reaction Pressure (psig) | Reaction Temp. (° C.) | Tertiary Butyl Alcohol Conversion (%) | Selectivity, (%) Isobutylene | Diisobutylene |
|---|---|---|---|---|---|
| 125 | 246 | 140 | 60.9 | 100.4 | 0.0 |
| 128 | 248 | 160 | 90.2 | 99.5 | 0.0 |
| 124 | 245 | 182 | 92.1 | 98.7 | 0.0 |

While the invention may be adaptable to various modifications and alternative forms, specific embodiments have been shown by way of example and described herein. However, it should be understood that the invention is not intended to be limited to the particular forms disclosed. Rather, the invention is to cover all modifications, equivalents, and alternatives falling within the spirit and scope of the invention as defined by the appended claims. Moreover, the different aspects of the disclosed compositions and methods may be utilized in various combinations and/or independently. Thus the invention is not limited to only those combinations shown herein, but rather may include other combinations. Furthermore, as used herein, the indefinite articles "a" and "an" connote "one or more."

REFERENCES

The following references, to the extent that they provide exemplary details supplementary to those set forth herein, are specifically incorporated herein by reference:

U.S. Pat. No 4,704,482
U.S. Pat. No 4,742,179
U.S. Pat. No 4,845,251
U.S. Pat. No 4,873,380

What is claimed is:

1. A method of producing isobutylene, comprising:
   contacting a feed stream that comprises tertiary butyl alcohol with a catalytically effective amount of a catalyst that consists essentially of Y-zeolite under conditions effective to produce isobutylene;
   wherein said Y-zeolite catalyst has a silica to alumina ratio of less than or equal to about 10,
   wherein said contacting occurs under conditions effective so that conversion of tertiary butyl alcohol is from about 80% to about 100%, and
   wherein selectivity to isobutylene is from about 85% to about 100%.

2. The method of claim 1, wherein said contacting comprises contacting said tertiary butyl alcohol with said Y-zeolite catalyst within a batch process reaction vessel.

3. The method of claim 1, said Y-zeolite catalyst has a silica to alumina ratio of from about 1 to about 10.

4. The method of claim 1, said Y-zeolite catalyst has a silica to alumina ratio of from about 5 to about 10.

5. The method of claim 1, said Y-zeolite catalyst has a silica to alumina ratio of from about 5 to about 6.

6. The method of claim 1, wherein said feed stream further comprises water.

7. The method of claim 1, wherein said feed stream comprises from about 70% to about 100% by weight tertiary butyl alcohol by total weight of said feed stream.

8. The method of claim 1, wherein said feed stream comprises from about 70% to less than about 100% by weight tertiary butyl alcohol by total weight of said feed stream, and from greater than about 0% to about 30% by weight water by total weight of said feed stream.

9. A method of producing isobutylene, comprising:
   contacting a feed stream comprising tertiary butyl alcohol and water with a catalyst that consists essentially of Y-zeolite to produce isobutylene;
   wherein said Y-zeolite catalyst has a silica to alumina ratio of less than or equal to about 10;
   wherein said contacting occurs within a reaction vessel at a temperature of greater than or equal to about 140° C., a pressure of from about 50 psig to 1000 psig, and a LHSV of from about 0.1 g/mL catalyst/hour to about 20.0 g/mL catalyst hour; and
   wherein conversion of tertiary butyl alcohol is from about 80% to about 100%, and wherein selectivity to isobutylene is from about 85% to about 100%.

10. The method of claim 9, wherein said contacting occurs at a temperature of from about 140° C. to about 250° C.

11. The method of claim 9, wherein said contacting occurs at a temperature of from about 140° C. to about 200° C.

12. The method of claim 9, wherein said contacting occurs at a temperature of from about 180° C. to about 250° C.

13. The method of claim 9, wherein said contacting occurs at a LHSV of from about 1 g/mL catalyst/hour to about 5 g/ml catalyst/hour.

14. The method of claim 9, wherein said contacting occurs at a pressure of from about 240 psig to about 275 psig.

15. The method of claim 9, wherein said contacting occurs under conditions effective so that selectivity to isobutylene is from about 90% to about 100%.

16. The method of claim 9, wherein said contacting occurs at a temperature of from about 200° C. to about 250° C. and wherein said conversion of tertiary butyl alcohol is from about 90% to about 100%.

17. The method of claim 16, wherein said contacting occurs at a temperature of from about 200° C. to about 250° C., wherein said conversion of tertiary butyl alcohol is from about 95% to about 100% and wherein said selectivity to isobutylene is from about 95% to about 100%.

18. The method of claim 9, wherein said contacting occurs at a temperature of from about 160° C. to about 250° C. and wherein said conversion of tertiary butyl alcohol is from about 90% to about 100%.

19. The method of claim 9, wherein said conversion of tertiary butyl alcohol is from about 90% to about 100%.

20. The method of claim 9, wherein said selectivity to isobutylene is from about 95% to about 100%.

21. The method of claim 20, wherein said conversion of tertiary butyl alcohol is from about 90% to about 100%.

22. The method of claim 9, wherein said Y-zeolite catalyst has a silica to alumina ratio of from about 1 to about 10.

23. The method of claim 9, wherein said Y-zeolite catalyst has a silica to alumina ratio of from about 5 to about 10.

24. The method of claim 9, wherein said Y-zeolite catalyst has a silica to alumina ratio of from about 5 to about 6.

25. A method of producing isobutylene, comprising:
contacting a feed stream comprising tertiary butyl alcohol and water with a catalyst that consists essentially of Y-zeolite to produce isobutylene;
wherein said Y-zeolite catalyst has a silica to alumina ratio of from about 5 to about 6;
wherein said contacting occurs within a reaction vessel at a temperature of from about 140° C. to about 200° C., a pressure of from about 240 psig to about 275 psig, and a LHSV of from about 1 g/mL catalyst/hour to about 5 g/mL catalyst/hour; and
wherein conversion of tertiary butyl alcohol is from about 80% to about 100%, and wherein selectivity to isobutylene is from about 85% to about 100%.

26. A method of producing isobutylene, comprising:
contacting tertiary butyl alcohol with a catalytically effective amount of catalyst consisting essentially of Y-zeolite under conditions effective to produce isobutylene;
wherein said Y-zeolite catalyst has a silica to alumina ratio of about 5 to about 6,
wherein said contacting occurs under conditions effective so that conversion of tertiary butyl alcohol is from about 80% to about 100%, and wherein selectivity to isobutylene is from about 85% to about 100%.

27. The method of claim 26, wherein said contacting comprises contacting said tertiary butyl alcohol with said Y-zeolite catalyst within a batch process reaction vessel.

28. The method of claim 26, wherein said contacting comprises contacting a feed stream with said Y-zeolite catalyst, said feed stream comprising said tertiary butyl alcohol.

29. The method of claim 28, wherein said feed stream further comprises water.

30. The method of claim 28, wherein said feed stream comprises from about 70% to about 100% by weight tertiary butyl alcohol by total weight of said feed stream.

31. The method of claim 28, wherein said feed stream comprises from about 70% to less than about 100% by weight tertiary butyl alcohol by total weight of said feed stream, and from greater than about 0% to about 30% by weight water by total weight of said feed stream.

32. A method of producing isobutylene, comprising:
contacting a feed stream with a catalytically effective amount of Y-zeolite catalyst under conditions effective to produce isobutylene, wherein the feed stream consists essentially of tertiary butyl alcohol and, optionally, water;
wherein said Y-zeolite catalyst has a silica to alumina ratio of less than or equal to about 10,
wherein said contacting occurs under conditions effective so that conversion of tertiary butyl alcohol is from about 80% to about 100%, and wherein selectivity to isobutylene is from about 85% to about 100%.

33. The method of claim 32, wherein said contacting comprises contacting the feedstream with the Y-zeolite catalyst within a batch process reaction vessel.

34. The method of claim 32, wherein the Y-zeolite catalyst has a silica to alumina ratio of from about 1 to about 10.

35. The method of claim 32, wherein the Y-zeolite catalyst has a silica to alumina ratio of from about 5 to about 10.

36. The method of claim 32, wherein the Y-zeolite catalyst has a silica to alumina ratio of from about 5 to about 6.

37. The method of claim 32, wherein the feed stream contains from about 70% to about 100% by weight tertiary butyl alcohol by total weight of the feed stream.

38. The method of claim 32, wherein the feed stream contains from about 70% to less than about 100% by weight tertiary butyl alcohol by total weight of the feed stream, and up to about 30% by weight water by total weight of the feed stream.

39. The method of claim 32, wherein the water is present in the feed stream.

* * * * *